(12) United States Patent
Shipp (10) Patent No.: US 7,678,125 B2
(45) Date of Patent: Mar. 16, 2010

(54) SURGICAL LIGATION CLIP

(75) Inventor: John I. Shipp, Jacksonville Beach, FL (US)

(73) Assignee: Apollo Camera, L.L.C., Estill Springs, TN (US)

( * ) Notice: Subject to any disclaimer, the term of this patent is extended or adjusted under 35 U.S.C. 154(b) by 958 days.

(21) Appl. No.: 10/706,715

(22) Filed: Nov. 12, 2003

(65) Prior Publication Data

US 2006/0129168 A1    Jun. 15, 2006

Related U.S. Application Data

(60) Provisional application No. 60/425,521, filed on Nov. 12, 2002.

(51) Int. Cl.
*A61B 17/08* (2006.01)
*B42F 1/02* (2006.01)

(52) U.S. Cl. .......... 606/157; 606/142; 606/151; 606/158; 24/67.9; 24/567

(58) Field of Classification Search ........... 606/142, 606/143, 151, 157, 158, 221, 232; 24/545–552, 24/67.1–67.9, DIG. 10, 67 R, 567; D19/65
See application file for complete search history.

(56) References Cited

U.S. PATENT DOCUMENTS

| | | | |
|---|---|---|---|
| 648,841 A | 5/1900 | Brosnan | |
| 1,332,287 A * | 3/1920 | Genevieve et. al. | 24/549 |
| 1,458,797 A | 6/1923 | Beale | |
| 1,666,514 A * | 4/1928 | Sigler | 24/546 |
| 2,113,991 A * | 4/1938 | Larsen | 24/549 |
| 2,498,372 A | 2/1950 | Kortlucke, Jr. et al. | |
| 2,626,608 A | 1/1953 | Garland | |
| 2,874,384 A | 2/1959 | Krone | |
| 2,876,778 A | 3/1959 | Kees, Jr. | |
| 3,023,039 A | 2/1962 | Henningsen et al. | |
| 3,023,468 A | 3/1962 | Hord et al. | |
| 3,032,039 A | 5/1962 | Beaty | |
| 3,056,408 A | 10/1962 | Brown | |
| 3,098,232 A | 7/1963 | Brown | |
| 3,120,230 A | 2/1964 | Skold | |
| 3,125,789 A * | 3/1964 | Parker | 24/67.9 |
| 3,270,745 A | 9/1966 | Wood | |
| 3,274,658 A | 9/1966 | Pile | |

(Continued)

FOREIGN PATENT DOCUMENTS

DE        2330182        1/1975

(Continued)

OTHER PUBLICATIONS

Papainoannou, Thanassis, M.S., Daykhovsky, Leon, M.D., Grundfest, Warren S., M.D.: "Safety Evaluation of Laproscopically Applied Clips": *Journal of Laproscopic Surgery* 1996: 6(2): 99-106.

(Continued)

*Primary Examiner*—Anhtuan T Nguyen
*Assistant Examiner*—Kathleen Sonnett
(74) *Attorney, Agent, or Firm*—Martin & Ferraro, LLP (57) ABSTRACT

A surgical ligation clip for double ligating a vessel, duct or other fluid carrying structure and a method for double ligating such structure.

32 Claims, 3 Drawing Sheets

U.S. PATENT DOCUMENTS

| | | |
|---|---|---|
| 3,363,628 A | 1/1968 | Wood |
| 3,439,522 A | 4/1969 | Wood |
| 3,439,523 A | 4/1969 | Wood |
| 3,476,114 A | 11/1969 | Shannon et al. |
| 3,518,993 A | 7/1970 | Blake |
| 3,631,707 A | 1/1972 | Miller |
| 3,675,688 A | 7/1972 | Bryan et al. |
| 3,683,927 A | 8/1972 | Noiles |
| 3,757,629 A | 9/1973 | Schneider |
| 3,777,538 A | 12/1973 | Weatherly et al. |
| 3,827,277 A | 8/1974 | Weston |
| 3,827,438 A | 8/1974 | Kees, Jr. |
| 3,882,854 A | 5/1975 | Hulka et al. |
| 3,911,923 A | 10/1975 | Yoon |
| 3,955,581 A | 5/1976 | Spasiano et al. |
| 3,989,049 A | 11/1976 | Yoon |
| 4,017,337 A | 4/1977 | Winter et al. |
| 4,024,868 A | 5/1977 | Williams |
| 4,027,510 A | 6/1977 | Hiltebrandt |
| 4,038,987 A | 8/1977 | Komiya |
| 4,041,931 A | 8/1977 | Elliot et al. |
| 4,064,881 A | 12/1977 | Meredith |
| 4,086,926 A | 5/1978 | Green et al. |
| 4,146,130 A | 3/1979 | Samuels et al. |
| 4,152,920 A | 5/1979 | Green |
| 4,169,476 A | 10/1979 | Hiltebrandt |
| 4,170,990 A | 10/1979 | Baumgart et al. |
| 4,196,836 A | 4/1980 | Becht |
| 4,217,902 A | 8/1980 | March |
| 4,226,239 A | 10/1980 | Polk et al. |
| 4,226,242 A | 10/1980 | Jarvik |
| 4,228,895 A | 10/1980 | Larkin |
| 4,241,734 A | 12/1980 | Kandel et al. |
| 4,242,902 A | 1/1981 | Green |
| 4,246,903 A | 1/1981 | Larkin |
| 4,274,415 A | 6/1981 | Kanamoto et al. |
| 4,299,224 A | 11/1981 | Noiles |
| 4,317,451 A | 3/1982 | Cerwin et al. |
| 4,340,061 A | 7/1982 | Kees, Jr. et al. |
| 4,349,028 A | 9/1982 | Green |
| 4,367,746 A | 1/1983 | Derechinsky |
| 4,372,316 A | 2/1983 | Blake, III et al. |
| 4,374,523 A | 2/1983 | Yoon |
| 4,396,139 A | 8/1983 | Hall et al. |
| 4,412,539 A | 11/1983 | Jarvik |
| 4,418,694 A | 12/1983 | Beroff et al. |
| 4,425,915 A | 1/1984 | Ivanov |
| 4,427,008 A | 1/1984 | Transue |
| 4,430,997 A | 2/1984 | DiGiovanni et al. |
| 4,433,689 A | 2/1984 | Von Zeppelin |
| 4,444,187 A | 4/1984 | Perlin |
| 4,448,193 A | 5/1984 | Ivanov |
| 4,449,530 A | 5/1984 | Bendel et al. |
| 4,450,839 A | 5/1984 | Transue |
| 4,450,840 A | 5/1984 | Mericle et al. |
| 4,471,766 A | 9/1984 | Terayama |
| 4,471,780 A | 9/1984 | Menges et al. |
| 4,476,865 A | 10/1984 | Failla et al. |
| 4,478,218 A | 10/1984 | Mericle |
| 4,478,220 A | 10/1984 | Di Giovanni et al. |
| 4,480,641 A | 11/1984 | Failla et al. |
| 4,485,816 A | 12/1984 | Krumme |
| 4,487,205 A | 12/1984 | Di Giovanni et al. |
| 4,492,232 A | 1/1985 | Green |
| 4,493,319 A | 1/1985 | Polk et al. |
| 4,500,024 A | 2/1985 | DiGiovanni et al. |
| 4,509,518 A | 4/1985 | McGarry et al. |
| 4,512,345 A | 4/1985 | Green |
| 4,527,562 A | 7/1985 | Mericle |
| 4,550,715 A | 11/1985 | Santangelo et al. |
| 4,556,058 A | 12/1985 | Green |
| 4,556,060 A | 12/1985 | Perlin |
| 4,557,263 A | 12/1985 | Green |
| 4,562,839 A | 1/1986 | Blake, III et al. |
| 4,569,346 A | 2/1986 | Poirier |
| 4,570,633 A | 2/1986 | Golden |
| 4,590,937 A | 5/1986 | Deniega |
| 4,616,650 A | 10/1986 | Green et al. |
| 4,616,651 A | 10/1986 | Golden |
| 4,620,541 A | 11/1986 | Gertzman et al. |
| 4,624,254 A | 11/1986 | McGarry et al. |
| 4,637,395 A | 1/1987 | Caspar et al. |
| 4,638,804 A | 1/1987 | Jewusiak |
| 4,646,741 A | 3/1987 | Smith |
| 4,658,822 A | 4/1987 | Kees, Jr. |
| 4,660,558 A | 4/1987 | Kees, Jr. |
| 4,662,373 A | 5/1987 | Montgomery et al. |
| 4,665,906 A | 5/1987 | Jervis |
| 4,671,278 A | 6/1987 | Chin |
| 4,674,504 A | 6/1987 | Klieman et al. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,741,337 A | 5/1988 | Smith et al. |
| 4,765,335 A | 8/1988 | Schmidt et al. |
| 4,777,949 A * | 10/1988 | Perlin ........................ 606/158 |
| 4,777,950 A * | 10/1988 | Kees, Jr. ..................... 606/158 |
| 4,788,966 A | 12/1988 | Yoon |
| 4,791,707 A | 12/1988 | Tucker |
| 4,796,625 A | 1/1989 | Kees, Jr. |
| 4,796,627 A | 1/1989 | Tucker |
| 4,799,481 A | 1/1989 | Transue et al. |
| 4,821,721 A | 4/1989 | Chin et al. |
| 4,822,348 A | 4/1989 | Casey |
| 4,834,096 A | 5/1989 | Oh et al. |
| 4,844,066 A | 7/1989 | Stein |
| 4,854,317 A | 8/1989 | Braun |
| 4,858,608 A | 8/1989 | McGuilkin |
| 4,869,268 A | 9/1989 | Yoon |
| 4,919,152 A | 4/1990 | Ger |
| 4,934,364 A | 6/1990 | Green |
| 4,943,298 A | 7/1990 | Fujita et al. |
| 4,944,443 A | 7/1990 | Oddsen et al. |
| 4,950,258 A | 8/1990 | Kawai et al. |
| 4,961,743 A | 10/1990 | Kees, Jr. et al. |
| 4,966,603 A | 10/1990 | Focelle et al. |
| 4,967,949 A | 11/1990 | Sandhaus |
| 4,976,722 A | 12/1990 | Failla |
| 4,979,950 A | 12/1990 | Transue et al. |
| 4,983,176 A | 1/1991 | Cushman et al. |
| 5,002,563 A | 3/1991 | Pyka et al. |
| 5,026,379 A | 6/1991 | Yoon |
| 5,030,226 A | 7/1991 | Green et al. |
| 5,035,692 A | 7/1991 | Lyon et al. |
| 5,037,433 A | 8/1991 | Wilk et al. |
| 5,044,540 A | 9/1991 | Dulebohn |
| 5,053,045 A | 10/1991 | Schmidt et al. |
| 5,084,057 A | 1/1992 | Green et al. |
| 5,100,420 A | 3/1992 | Green et al. |
| 5,156,608 A | 10/1992 | Troidl et al. |
| 5,156,609 A | 10/1992 | Nakao et al. |
| 5,171,249 A | 12/1992 | Stefanchik et al. |
| 5,171,250 A | 12/1992 | Yoon |
| 5,190,203 A | 3/1993 | Rodak |
| 5,192,288 A | 3/1993 | Thompson et al. |
| 5,197,970 A | 3/1993 | Green et al. |
| 5,207,692 A | 5/1993 | Kraus et al. |
| 5,217,473 A | 6/1993 | Yoon |
| 5,242,456 A | 9/1993 | Nash et al. |
| 5,257,713 A | 11/1993 | Green et al. |
| 5,290,299 A | 3/1994 | Fain et al. |
| 5,300,081 A | 4/1994 | Young et al. |
| 5,340,360 A | 8/1994 | Stefanchik |

| | | |
|---|---|---|
| 5,342,373 A | 8/1994 | Stefanchik et al. |
| 5,364,002 A | 11/1994 | Green et al. |
| 5,366,134 A | 11/1994 | Green et al. |
| 5,368,600 A | 11/1994 | Failla et al. |
| 5,383,880 A | 1/1995 | Hooven |
| 5,389,098 A | 2/1995 | Tsuruta et al. |
| 5,395,381 A | 3/1995 | Green et al. |
| 5,431,668 A | 7/1995 | Burbank, III et al. |
| 5,431,669 A | 7/1995 | Thompson et al. |
| 5,439,468 A | 8/1995 | Schulze et al. |
| 5,474,567 A | 12/1995 | Stefanchik et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,527,318 A | 6/1996 | McGarry |
| 5,527,319 A | 6/1996 | Green et al. |
| D372,937 S * | 8/1996 | Anders ............... D19/65 |
| 5,542,949 A | 8/1996 | Yoon |
| 5,547,474 A | 8/1996 | Kloeckl et al. |
| 5,593,414 A * | 1/1997 | Shipp et al. ............... 606/142 |
| 5,601,573 A | 2/1997 | Fogelberg et al. |
| 5,601,574 A | 2/1997 | Stefanchik et al. |
| 5,620,452 A | 4/1997 | Yoon |
| RE35,525 E | 6/1997 | Stefanchik et al. |
| 5,653,720 A | 8/1997 | Johnson et al. |
| 5,681,330 A | 10/1997 | Hughett et al. |
| 5,695,502 A | 12/1997 | Pier et al. |
| 5,700,270 A | 12/1997 | Peyser et al. |
| 5,700,271 A | 12/1997 | Whitfield et al. |
| 5,702,408 A | 12/1997 | Wales et al. |
| D401,626 S * | 11/1998 | Shyu ............... D19/65 |
| 5,833,700 A | 11/1998 | Fogelberg et al. |
| 5,843,097 A | 12/1998 | Mayenberger et al. |
| 5,849,019 A | 12/1998 | Yoon |
| 5,855,590 A | 1/1999 | Malecki et al. |
| 5,858,018 A * | 1/1999 | Shipp et al. ............... 606/142 |
| 5,897,565 A | 4/1999 | Foster |
| 5,921,997 A | 7/1999 | Fogelberg et al. |
| 5,993,465 A | 11/1999 | Shipp et al. |
| 6,139,555 A | 10/2000 | Hart et al. |
| 6,159,223 A | 12/2000 | Danks et al. |
| 6,193,732 B1 | 2/2001 | Frantzen et al. |
| 6,226,843 B1 * | 5/2001 | Crainich ............... 24/545 |
| 6,290,575 B1 * | 9/2001 | Shipp ............... 451/28 |
| 6,350,269 B1 | 2/2002 | Shipp et al. |
| 6,464,710 B1 | 10/2002 | Foster |
| 6,652,539 B2 | 11/2003 | Shipp et al. |
| 6,652,545 B2 | 11/2003 | Shipp et al. |

FOREIGN PATENT DOCUMENTS

| | | |
|---|---|---|
| DE | 3722311 | 1/1989 |
| DE | 3802651 | 8/1989 |
| DE | 4015562 | 11/1991 |
| JP | 6-237939 | 8/1994 |
| SU | 1389762 | 4/1988 |
| WO | WO 90/03763 | 4/1990 |

OTHER PUBLICATIONS

Nelson, Timothy M., M.D., Nakashima, Masanobu, M.D., Mulvihill, Sean J., M.D.: "How Secure Are Laproscopically Placed Clips? An In Vitro and In Vivo Study": *Arch Surg*. 1992: 127: 718-720: pub. Dec. 8, 1991.

Amaud, Jean-Pierre, M.D., Bergamaschi, Roberto, M.D.,: "Migration and Slipping of Metal Clips After Celioscopic Cholecystomy": *Surgical Laproscopy & Endoscopy* 1993: 3(6): 487-488: pub. 1993 Raven Press, Ltd., New York.

Klein, R.D., Jessup, G., Ahari, F., Connolly, R.J., Schwaitzberg, S.D.: "Comparison of titanium and absorbable polymeric surgical clips for use in laproscopic cholecystomy": *Surgical Endoscopy* 1994: pub. 1994 Springer-Verlag New York Inc.

* cited by examiner

SURGICAL LIGATION CLIP

RELATED APPLICATIONS

This application claims the benefit of U.S. Provisional Application No. 60/425,521, filed Nov. 12, 2002, the disclosure of which is incorporated by reference herein.

BACKGROUND OF THE INVENTION

1. Field of the Invention

The present invention relates generally to mechanical devices used in surgical procedures to obtain ligation or hemostasis and more particularly, to a ligation clip used during surgery to clamp vessels or ducts such as a cystic artery or cystic duct and thereby obtain ligation.

2. Description of the Prior Art

It will be appreciated by those skilled in the art that the use of ligation clips to control bleeding during surgical procedures is well known. As described, for example, in U.S. Pat. Nos. 4,976,722 and 4,979,950, prior art clips are generally formed of metal wire usually a titanium alloy having a U-shaped cross section. Such prior art clips often include a grooved pattern machined into the inner or clamping surfaces of the clip in an attempt to enhance the ability of the clip to remain in position after it is closed around the vessel. Application of the clip to the vessel is often effected by means of a crushing action produced by a clip applier such as that disclosed in U.S. Pat. No. 5,030,226. Such crushing action permanently deforms the clips making them difficult to remove or reposition.

Prior art surgical ligation clips have several inherent problems. For example, the force applied by the clip to the vessel can be variable and inconsistent from one clip to the next because of the variation in crushing force applied to the clip by the user. Further, prior art clips have a tendency to slip off the end of the blood vessel stub (i.e., perpendicular to the axis of the vessel) to which it has been applied because of the low coefficient of friction associated with the clip and lack of adequate restraining force provided by the clip. Because of this, separation of the clip from the vessel to which it has been applied after the wound has been closed is not uncommon. A related problem found in the prior art is the fact that the ligation or restraining force offered by crushed clips vary along the length of the clip decreasing toward the open end. Thus, the section of the vessel near the open end of the clip can be inadequately ligated.

It is also common in the prior art to form and crush the clip only at the time of its application to the targeted vessel. In order to ligate a vessel with a crush clip, it is required that the inside clearance dimension of the clip prior to crushing be larger than the vessel. This does not lend itself to clip appliers designed to pass through small 5 mm trocars. The applier must be inserted through a trocar placed through the patient's external tissues and into the surgical field. Thus, prior art ligation clip appliers used in laparoscopic procedures typically consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm or even a 2.5 mm diameter port is highly desirable. One approach for providing a smaller diameter endoscopic clip applier is disclosed in U.S. Pat. No. 5,601,573 to Fogelberg et al. The '573 patent applies a complex manipulation to advance the clip in a closed position and then open the clip prior to placement. To place a clip, the '573 patent uses an overly complex multi-stage trigger mechanism for actuating a clamping jaw and advancing the clip.

The clip described in the '573 patent is a spring-action clip that suffers from several deficiencies. First, the clip has little or no pre-load, which means that vessels or ducts of very small diameter have little or no ligation force applied. Vessels such as cystic arteries often fall into this small category. Secondly, the clip of the '573 patent provides for only a single point of contact of the clip on the vessel. This requires a surgeon to use multiple clips to ensure ligation in case one clip is dislodged from the vessel by activity of the patient during a post-surgery period. The clip of the '573 patent is also very narrow in width and thereby has little or no utility for ligating vessels or torn tissue in an end-on or head-on application technique such as described in U.S. Pat. No. 6,350,269 to Shipp et al.

The '269 patent describes a clip that has many advantages for use in trocar entry wounds of 5 mm and smaller. The '269 clip includes a vessel clamping arm, a vessel support member, and tension coils integrally joining the arm and support member. The vessel support member includes two legs that are substantially parallel and joined by a bend section at the distal end of the clip. The vessel clamping arm includes a single leg with a bend section at the distal-most end of the clip and terminates at the free end of the single wire forming the clip at a point between the distal and proximal most ends of the clip. Thus, the side of the clip of the '269 patent which contains the single leg of the clamping arm may subject the vessel being ligated to greater shear than necessary. The clip shown in FIG. 9 of the '269 patent can provide inadequate ligation for very small vessels that can be woven between the legs of the vessel support member and the leg of the clamping member because of spaces between these three legs. The clip described in the '269 patent is not symmetric in applying a ligating force passing through the clip parallel to the longitudinal axis. Thus, when the clip is loaded into a clip applier, care must be taken to ensure that the clip is loaded in the proper orientation.

Many clips of the prior art have an exposed free end which is small in dimension and can be caught or snagged on tissue during either the clip placement procedure or when in some circumstances the clip has to be removed. The clip of the '573 patent and the crush clips of the prior art are examples of clips that can snag tissue upon installation. The clip of the '269 patent has a free end generally pointed in the proximal direction and is an example of a clip that could snag tissue upon a removal procedure.

What is needed then is a spring-loaded ligation clip with a pre-load that supplies a ligating force to very thin vessels that has two points of ligation throughout the usable length of the clip. What is also needed is a spring clip having ligating members that do not interfere with tissue during the installation process so that tissues of varying thicknesses can be ligated throughout the usable length of the clip. What is further needed is a clip that does not have a free end that could snag and become entangled in tissue during installation or removal procedures. What is also needed is a clip with upper and lower support members that are symmetric to reduce or eliminate loading errors. A clip that satisfies one or more of these needs is described.

Further objects, features, and advantages of the present invention will be readily apparent to those skilled in the art upon a reading of the following disclosure when taken in conjunction with the accompanying drawings.

SUMMARY OF THE INVENTION

The present invention in one preferred embodiment is directed to a surgical ligation clip for ligating a fluid carrying structure. The clip includes an upper support member oriented generally along the mid-longitudinal axis of the clip, a lower support member oriented generally along the mid-longitudinal axis of the clip, and a connector that joins the upper and lower support members at the proximal end of the clip. The clip is formed of a single piece of wire having a first free end and a second free end that each terminate proximate the proximal end of the clip.

Another preferred embodiment of the surgical ligation clip includes an upper support member and a lower support member that are each oriented generally along the mid-longitudinal axis of the clip between the proximal and distal ends of the clip, and a connector at the proximal end of the clip that joins the upper and lower support members. The clip is formed of a single piece of material having a first free end and a second free end that each terminate proximate the proximal end of the clip. At least one of the free ends face in a direction that is at least one of transverse to the mid-longitudinal axis of the clip and away from the proximal end of the clip.

In another embodiment the present invention includes a method of ligating a fluid carrying structure which includes the steps of inserting into a body cavity of a patient a ligation clip having two free ends that terminate proximate the proximal end of the ligation clip; placing the ligation clip in an open position around at least a portion of the fluid carrying structure; and double ligating the fluid carrying structure with the clip.

It is to be understood that both the foregoing general description and the following detailed description are exemplary and explanatory only and are not restrictive of the invention, as claimed. The accompanying drawings, which are incorporated in and constitute a part of this specification, illustrate exemplary embodiments of the invention and together with the description, serve to explain the principles of the invention.

DETAILED DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Referring now to the drawings and particularly to FIGS. 1 to 5, a surgical spring clip is shown and generally designated by the numeral 100. Clip 100 has a proximal end 102 and a distal end 104 opposite proximal end 102 along the mid-longitudinal axis of clip 100. Clip 100 includes an upper vessel support member 106 and a lower vessel support member 108. Upper and lower support members 106, 108 are joined together by a coil 110 at proximal end 102.

Coil 110 includes a first coil loop 112, a second coil loop 114, and an interior 116. First coil loop 112 is oriented generally parallel to the vertical longitudinal plane of clip 100. Second coil loop 114 is integrally joined to first coil loop 112 and is oriented generally at an angle to the vertical longitudinal plane of clip 100. First and second coil loops 112, 114 may be oriented at other angles relative to the vertical longitudinal plane or each other without departing from the broad scope of the present invention. Other forms of connectors may be used in lieu of coil 110 to join upper and lower support members 106, 108 together. For example only, upper and lower members 106, 108 may be connected by a bend section without any coils, by a single coil loop, or by more than two coil loops.

Upper support member 106 includes a first leg 118 connected to second leg 120 by an enlarged loop section 122. First leg 118 terminates in a first free end 124 proximate proximal end 102 of clip 100. Second leg 120 is joined to first coil loop 112 of coil 110. First and second legs 118, 120 of upper support member 106 are preferably parallel to one another and to the mid-longitudinal axis along a majority, and more preferably, along a substantial portion of the length of clip 100. First and second legs 118,120 have a recess that is preferably wide enough to accommodate the thickness of second coil 114 therein.

Lower support member 108 includes a first leg 126 connected to a second leg 128 by an enlarged loop section 130. First leg 126 is joined to second coil loop 114 of coil 110. Second leg 128 terminates in a second free end 132 proximate proximal end 102 of clip 100. First and second legs 126, 128 of lower support member 108 are preferably parallel to one another and to the mid-longitudinal axis along a majority, and more preferably, along a substantial portion of the length of clip 100. First and second legs 126, 128 have a recess that is preferably wide enough to accommodate the thickness of second coil 114 therein.

First and second legs 118, 120 of upper support member 106 are oriented to generally overlie first and second legs 126, 128, of lower support member 108. The general longitudinal alignment of the pair of legs of upper and lower support members 106, 108 provides a double ligation that is suitable for ligating small vessels. The leg pair configuration also provides a symmetry to the clip that reduces loading errors should the clip be loaded into a magazine for deployment.

Upper and lower support members 106, 108 each preferably have a vessel contacting surface oriented toward one another for gripping a fluid carrying structure therebetween. The gripping force of the vessel contacting surfaces may be enhanced by adding a series of ridges, notches, burrs by machining, etching, or other surface enhancing treatment.

It will be appreciated that the legs of upper and lower support members 106, 108 may curve in either or both the horizontal longitudinal plane or the vertical longitudinal plane. For example, in the horizontal longitudinal plane, first and second legs 118, 120 of upper support member 106 may be curved outwardly relative to the mid-longitudinal axis of clip 100 so as to create a larger recess proximate to the center of the clip. In the vertical longitudinal plane, upper and lower members 106, 108 may be curved so that the support members are in a generally convex or concave shape. Such a configuration can be beneficial where the surgical procedure involves a shape-sensitive tissue or bone structure.

First leg 118 of upper support member 106 and second leg 128 of lower support member 108 are each preferably provided with a pre-load force such that free ends 124, 132 are held inside interior 116 of coil 110 and the width dimension at proximal end 102 as measured perpendicular or transverse to the mid-longitudinal axis of clip 100 is minimized. A pre-load force is built into the clip by virtue of the bends between first and second coils 112, 114 and second leg 120 of upper support member 106 and first leg 126 of lower support member 108. Thus, the vessel contacting surfaces formed by the upper and lower vessel support members are held together with the force dictated by the torsion force in coil springs 112, 114. Preferably, a preload force is imposed on upper and lower support members 106, 108 so that the magnitude of the force is greater than necessary to move upper and lower members 106, 108 into contact.

Figure 5:
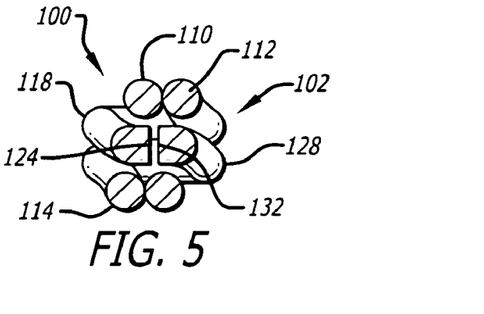
FIG. 5 is a cross sectional trailing end view taken along lines 5-5 of FIG. 2.

As shown in FIG. 5, portions of first leg 118 of upper support member 106 and second leg 128 of lower support member 108 are bent into an approximate 90 degree angle relative to the mid-longitudinal axis of clip 100 such that free ends 124, 132 face each other when the legs 118, 128 terminate inside interior 116 of coil 110. Orienting free ends 124, 132 toward one another provides several advantages, for example, reduced risk of snagging of tissue during clip insertion and removal procedures and a reduction in size of the clip, which is beneficial for minimally invasive procedures.

It will be understood that free ends 124, 132 may be oriented relative to the mid-longitudinal axis in a number of ways while still remaining within the scope of the present invention. For example, the free ends may be off-set vertically relative to one another so that the bend section of one of the legs overlies the bend section of another of the legs in a vertical plane transverse to the mid-longitudinal axis of clip 100. The free ends may be off-set horizontally relative to one another so that the bend section of the legs at proximal end 102 are in a side-by-side relationship in a horizontal plane transverse to the mid-longitudinal axis of clip 100. The free ends may also be offset relative to the vertical longitudinal plane such that one or both bend sections extend substantially the entire distance through interior 116 of coil 110. The free ends may also be configured to face away from one another, for example, along a plane transverse to the mid-longitudinal axis of clip 100. The free ends may face the same direction, for example, toward distal end 104 of clip 100. The direction that the free ends face need not be confined to a single plane. For example, one of the free ends may be oriented at an angle of 90 degrees relative to the other of the free ends.

The shape of each free end may be flat or curved, for example, dome-shaped. One of the free ends may have a convex shape to cooperatively engage an opposed free end having a concave shape. Such a configuration enhances the stability of the free ends.

Figure 6:
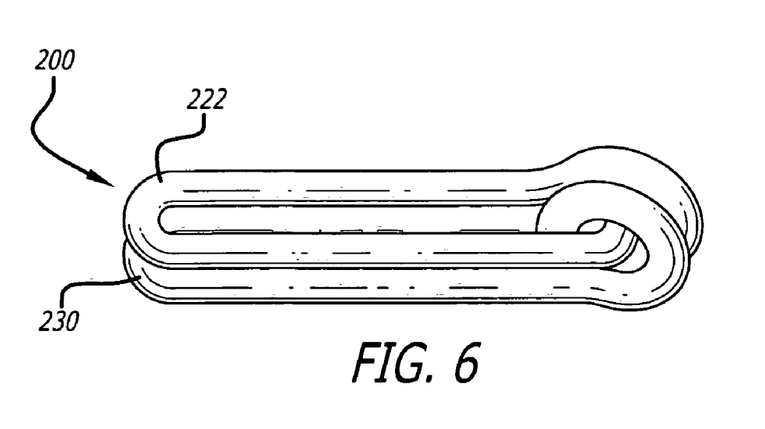
FIG. 6 is a perspective view of a clip in accordance with another preferred embodiment of the present invention.
Figure 7:
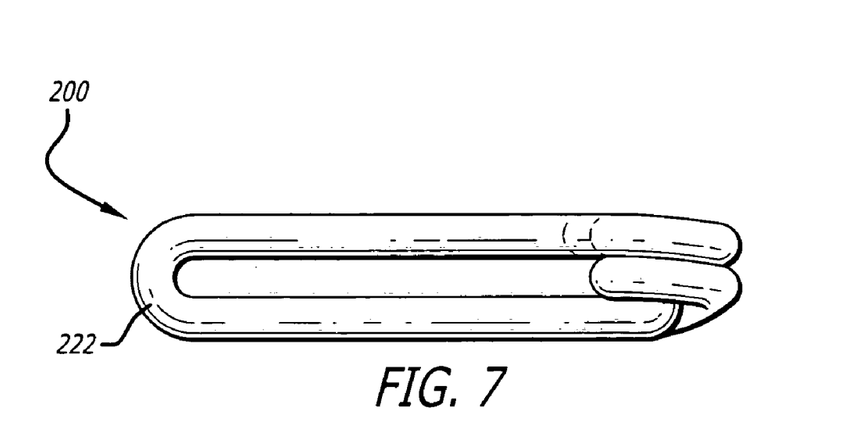
FIG. 7 is a top elevation view of a clip of FIG. 6.
Figure 8:
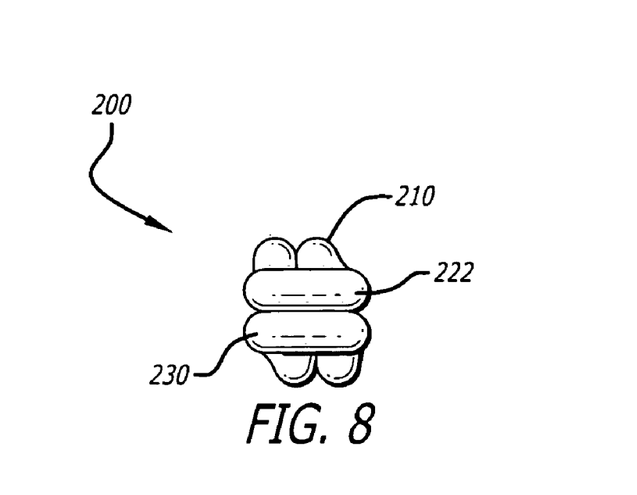
FIG. 8 is a front elevation view of the clip of FIG. 6.

FIGS. 6 to 8 show a second preferred embodiment of a clip of the present invention generally referred to by the reference number 200. Clip 200 operates in a similar way to clip 100 shown in FIGS. 1 to 5 except that enlarged loop sections 122, 130 are replaced by substantially parallel loop sections 222, 230 as shown in FIG. 8. The reduced width of parallel loop sections 222, 230 provides the added advantage of reducing the over-all width of the clip. Additionally, the parallel loop sections have an inner and external side surface configuration that is generally parallel to one another along the longitudinal axis of the clip. In this manner, more of the interior space of the loops is occupied as compared to the embodiment of FIG. 1. It will be understood that the features described in relation to clip 100 are generally applicable to clip 200 while still remaining within the broad scope of the present invention.

Figure 1:
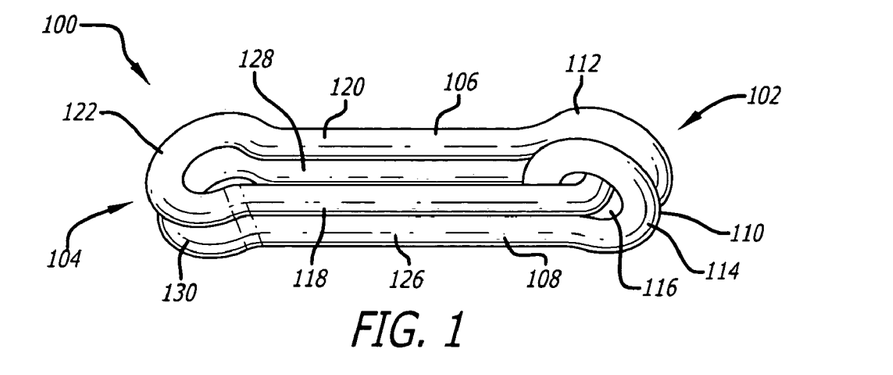
FIG. 1 is a perspective view of a clip in accordance with one preferred embodiment of the present invention.
Figure 2:
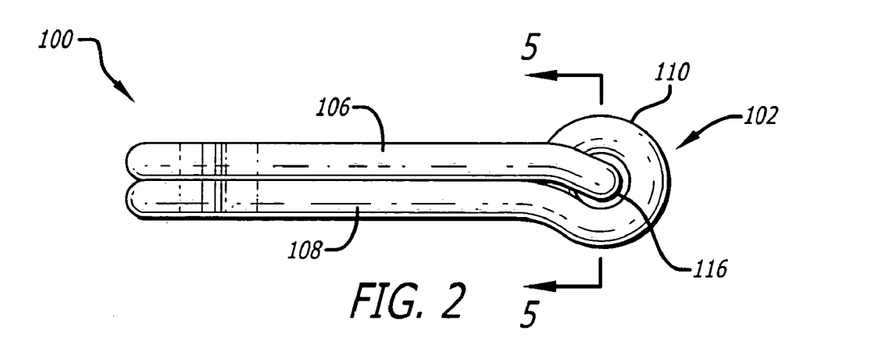
FIG. 2 is a side elevation view of the clip of FIG. 1.
Figure 3:
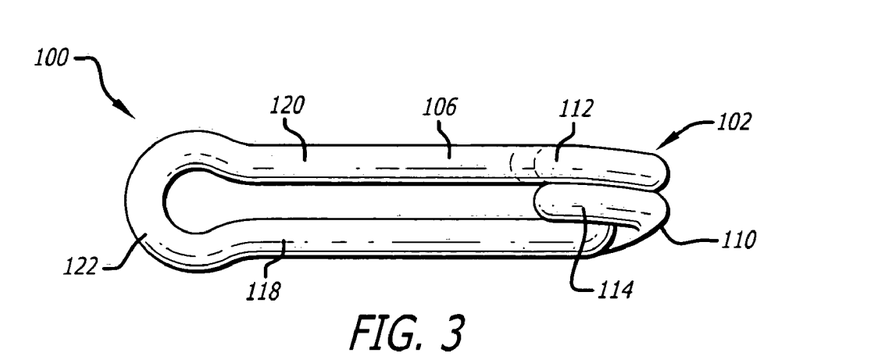
FIG. 3 is a top elevation view of the clip of FIG. 1.
Figure 4:
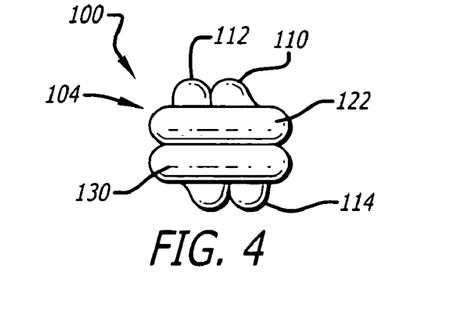
FIG. 4 is a front elevation view of the clip of FIG. 1.

The spring action of the clips of the present invention may be characterized using the equations of The Machinery's Handbook, pages 347-359, and The Associated Spring Design Handbook, pages 61-65. The spring clips described in both embodiments of the present invention are preferably compound springs. With reference to FIG. 1, upper and lower support members 106, 108 are held into contact by virtue of the torsion coils 112, 114 as described in the above references. In addition, loop sections 122, 130 also serve as torsion coil biases. Loop section 122 supplies the torsion force for first leg 118 of upper support member 106. If upper and lower support members 106, 108 are separated, a restoring force generated by coil 110 is provided by virtue of first and second coils 112, 114. Similarly, if first leg 118 of upper support member 106 and second leg 128 of lower support member 108 are moved in a plane perpendicular to the mid-longitudinal axis of the clip 100, loop sections 122, 130 will supply a restoring force that tends to move the legs back into the original parallel position. Thus, the spring clip of both the first and second embodiment is preferably a compound torsion coil with torsion bias loops supplying restoring forces into perpendicular axes. The spring clip in both the first and second embodiments are shown in the equilibrium position in FIGS. 1 and 6. In this state, the clips have been formed so that a pre-loaded force exists in each of the two orthogonal axes described above.

Upper and lower support members 106, 108 may be moved to a closed position to ligate a fluid carrying structure without imposing a preload on the clip. For example, upper and lower members 106, 108 may be adapted to be clamped by a separate device, or clip 100 may be formed of a conventional shape memory material.

Having described the apparatus, methods for its use will now be described. It should be understood that the order in which the method is performed is only preferred and that the steps may be performed in other orders while still remaining within the scope of the present invention. Additionally, some steps may be repeated as necessary C or omitted.

A preferred method for performing a surgical procedure with a clip includes inserting a ligation clip into a body cavity of a patient through a cannula preferably having a maximum diameter of 5 mm or less. The clip is preferably inserted using a clip applier such as described in U.S. Pat. No. 5,858,018, filed Oct. 3, 1994, or U.S. Pat. No. 6,350,269, filed Mar. 1, 1999, the disclosures of both of being incorporated herein by reference.

Before placing a clip completely on a vessel or other fluid carrying structure, the vessel is preferably preclamped so that the diameter of the vessel is reduced to a sufficient point where the maximum clearance between the upper and lower support members will permit the vessel to be between the support members. The clip is then placed in an open position about the vessel and allowed to move to the closed position to create a double ligation.

Figure 9:
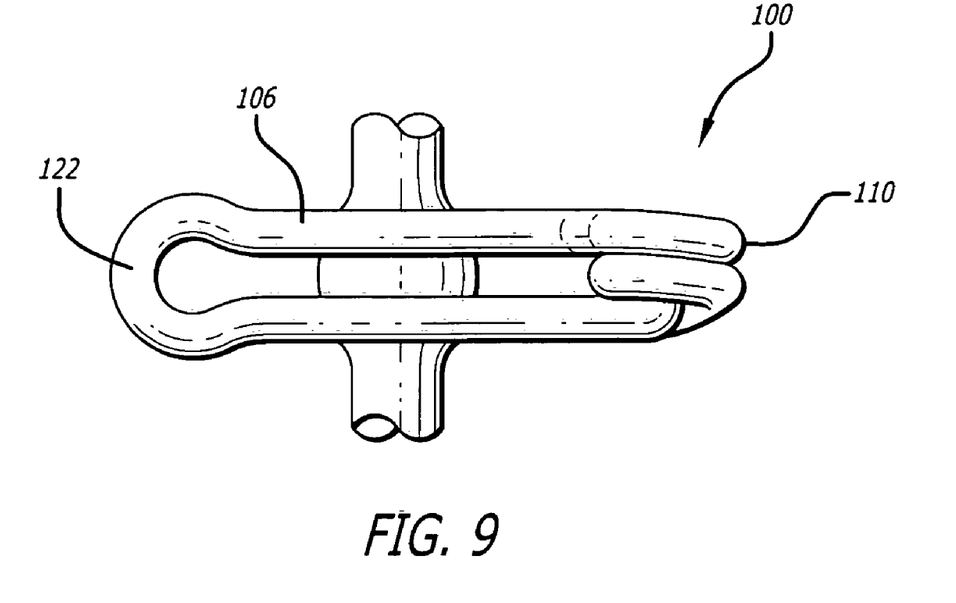
FIG. 9 is a top elevation view of the clip of FIG. 1 ligating a vessel.
Figure 10:
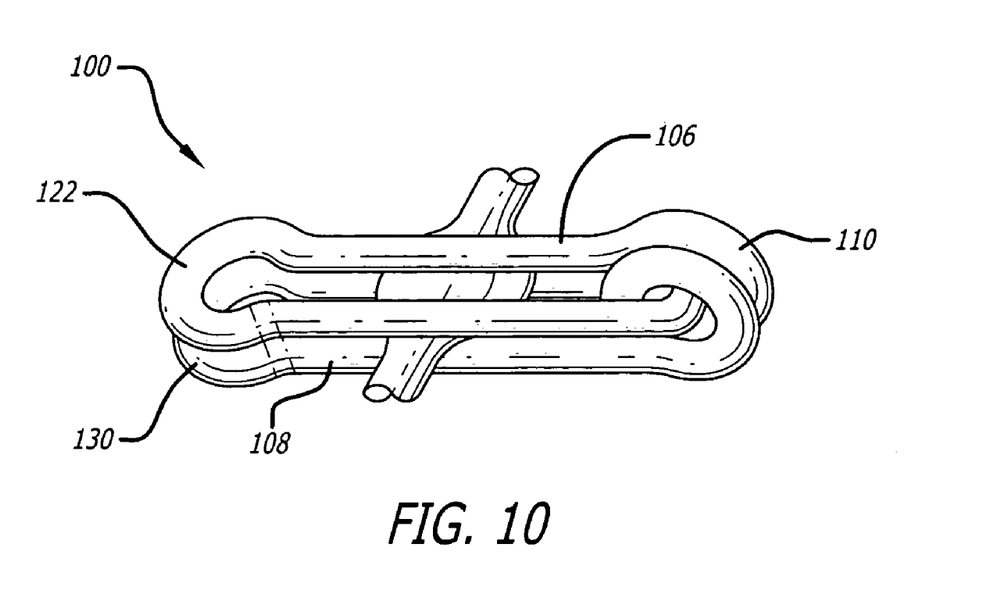
FIG. 10 is a perspective view of the clip of FIG. 1 ligating a vessel.

FIGS. 9 and 10 show a vessel that has been double-ligated by clip 100. The longitudinal arms of upper and lower support members 106, 108 generally overlie one another and ligate the vessel with minimal shear forces.

The method of the present invention is also suitable for ligating a stub end of a lumen. It will be appreciated by those skilled in the art that sometimes instead of placing clip 100 transversely across the length of a vessel as illustrated in FIGS. 9 and 10, it will be desirable to approach a stub end of a lumen head-on. With prior art clip designs this can be very difficult. This can be accomplished with clip 100 owing to the transverse width of loop sections 122, 130 which provide clamping surfaces that are the forward portions of loop sections 122, 130.

The clips of the present invention are preferably made of a single material. It will be appreciated that various combinations of materials may be used while still remaining within the scope of the present invention. A suitable material from which the clips of the present invention can be formed is wrought titanium 6A1-4V ELI alloy wire having a nominal diameter of 0.75 mm, and which meets ASTM Standard F136-92. The clips may also be formed of a conventional shape memory material.

The clips can be made of wire having a non-circular cross section, or formed from wire having a combination of circular and non-circular sections. For example, coil 110 and/or support members 106, 108 could be stronger if formed from wire having a square or rectangular-shaped cross section.

The clips of the present invention preferably have a maximum dimension transverse to the mid-longitudinal axis of the clip in the closed position of approximately 5 mm so as to be available for use in procedures utilizing 5 mm or smaller cannulas.

With reference to FIG. 1, the outer diameter of either of loop sections 122, 130 may be generally equal to or greater than the outer diameter of either of first and second coil loops 112, 114. It will be appreciated that the outer diameter of loop sections 122, 130 may be generally equal or different. Further, the loop sections at the distal end of the clips shown in FIGS. 1 and 6 may have other shapes without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A surgical ligation clip for ligating a fluid carrying structure, said clip comprising:
    a mid-longitudinal axis, a distal end, a proximal end opposite said distal end, a maximum clip length between said distal and proximal ends, a maximum clip height perpendicular to said maximum clip length, and a maximum clip width perpendicular to said maximum clip length and said maximum clip height, said maximum clip length being greater than twice said maximum clip height;
    an upper support member oriented generally along the mid-longitudinal axis of said clip, said upper support member having a maximum width adjacent said distal end perpendicular to the mid-longitudinal axis in a first plane generally parallel to the mid-longitudinal axis, and having a width less than said maximum width thereof in the first plane over a majority of the length of said clip between said distal and proximal ends;
    a lower support member oriented generally along the mid-longitudinal axis of said clip, said lower support member having a maximum width adjacent said distal end perpendicular to the mid-longitudinal axis in a second plane generally parallel to the mid-longitudinal axis, and having a width less than said maximum width thereof in the second plane over a majority of the length of said clip between said distal and proximal ends; and
    a connector at said proximal end of said clip joining said upper and lower support members, said connector having a maximum width perpendicular to the mid-longitudinal axis in a third plane generally parallel to the mid-longitudinal axis, and a maximum connector height in a fourth plane perpendicular to the mid-longitudinal axis and the third plane, said maximum connector height being equal equal to said maximum clip height, wherein said clip is formed of a single piece of wire having a substantially uniform thickness, said connector is formed of multiple coil windings of said single piece of wire, said coil windings of said connector have an interior and are unwound when moving said clip from a closed position to an open position, and said clip has a first free end and a second free end, each of said first and second free ends terminating proximate said proximal end, the first plane, the second plane, and the third plane are parallel to one another, at least one of said maximum width of said upper support member and said maximum width of said lower support member is greater than said maximum width of said connector, said distal end has a distal height parallel to said maximum clip height and said proximal end has a proximal width parallel to said maximum clip width, and each of said distal height and said proximal width is twice the thickness of said wire wherein said first end and said second end each terminates inside said interior of said coil.

2. The clip of claim 1, wherein said wire has a maximum thickness less than or equal to 1.0 mm.

3. The clip of claim 1, wherein said connector is adapted to bias said upper and lower support members toward one another in the closed position.

4. The clip of claim 1, wherein said connector is adapted to apply a force to said upper and lower support members to bias said upper and lower support members toward one another in the closed position, the force being greater than that needed to move said upper and lower members into contact with one another.

5. The clip of claim 1, wherein said upper and lower support members each include a loop at said distal end.

6. The clip of claim 1, wherein said upper and lower support members each have two parallel longitudinal members with a recess therebetween, said longitudinal members of said upper support member being adapted to generally overlie said longitudinal members of said lower members.

7. The clip of claim 6, wherein said longitudinal members of at least one of said upper and lower members extend along a substantial portion of the length of said clip.

8. The clip of claim 1, in combination with a clip applier for applying the clip to the fluid carrying structure.

9. The clip of claim 8, wherein said clip applier includes a magazine adapted to hold a plurality of clips.

10. The clip of claim 1, wherein at least one of said upper support member and said lower support member is enlarged adjacent said distal end of said clip.

11. The clip of claim 1, wherein each of said upper support member and said lower support member is formed of a first leg and a second leg.

12. The clip of claim 11, wherein said first leg and said second leg extend generally parallel to one another from said connector.

13. The clip of claim 12, wherein a gap is formed between said first leg and said second leg, and said gap has a width approximately equal to the thickness of said wire.

14. The clip of claim 1, wherein said clip has a minimum clip width perpendicular to said maximum clip length and said maximum clip height, and said connector has a minimum connector width in the third plane, said minimum connector width being equal to said minimum clip width.

15. The clip of claim 1, wherein said upper support member is connected to an upper portion of said connector and said lower support member is connected to a lower portion of said connector so that said coil windings are unwound when opening said clip.

16. A surgical ligation clip for ligating a fluid carrying structure, said clip comprising:
a mid-longitudinal axis, a distal end, a proximal end opposite said distal end, a maximum clip length between said distal and proximal ends, a maximum clip height perpendicular to said maximum clip length, and a maximum clip width and a minimum clip width perpendicular to said maximum clip length and said maximum clip height, said maximum clip length being greater than twice said maximum clip height;
an upper support member oriented generally along the mid-longitudinal axis of said clip between said proximal and distal ends of said clip, said upper support member having a maximum width adjacent said distal end perpendicular to the mid-longitudinal axis in a first plane generally parallel to the mid-longitudinal axis, and having a width less than said maximum width thereof in the first plane over a majority of the length of said clip between said distal and proximal ends;
a lower support member opposite said upper support member in a vertical plane parallel to the mid-longitudinal axis, said lower support member being oriented generally along the mid-longitudinal axis of said clip between said proximal and distal ends of said clip, said lower support member having a maximum width adjacent said distal end perpendicular to the mid-longitudinal axis in a second plane generally parallel to the mid-longitudinal axis, and having a width less than said maximum width thereof in the second plane over a majority of said clip between said distal and proximal ends; and
a connector at said proximal end of said dip joining said upper and lower support members, said connector having a maximum connector width and a minimum connector width, said maximum connector width and said minimum connector width both being perpendicular to the mid-longitudinal axis in a third plane generally parallel to the first and second planes and the mid-longitudinal axis, said minimum connector width is equal to said minimum clip width, wherein said clip is formed of a single piece of material having a substantially uniform thickness with a first free end and a second free end terminating proximate said proximal end, and at least one of said free ends facing in a direction that is at least one of transverse to the mid-longitudinal axis of said clip and away from said proximal end of said clip, said connector is formed of multiple coil windings of said single piece of material, said coil windings of said connector have an interior and are unwound when moving said clip from a closed position to an open position, at least one of said maximum width of said upper support member and said maximum width of said lower support member is greater than said maximum width of said connector, said distal end has a distal height parallel to said maximum clip height and said proximal end has a proximal width parallel to said maximum clip width, and each of said distal height and said proximal width is twice the thickness of said material wherein said first end and said second end each terminates inside said interior of said coil.

17. The clip of claim 16, wherein at least one of said free ends faces a direction generally transverse to the mid-longitudinal axis of said clip.

18. The dip of claim 16, wherein at least one of said free ends faces generally towards said distal end of said clip.

19. The clip of claim 16, wherein said first end and said second end each face away from said proximal end of said clip.

20. The clip of claim 16, wherein said connector is adapted to bias said upper and lower support members toward one another in the closed position.

21. The clip of claim 16, wherein said connector is adapted to apply a force to said upper and lower support members to bias said upper and lower support members toward one another in the closed position, the force being greater than that needed to move said upper and lower members into contact with one another.

22. The clip of claim 16, wherein said upper and lower support members each include a loop at said distal end.

23. The clip of claim 16, wherein said upper and lower support members each have two parallel longitudinal members with a recess therebetween, said longitudinal members of said upper support member being adapted to generally overlie said longitudinal members of said lower members.

24. The clip of claim 23, wherein said longitudinal members of at least one of said upper and lower members extend along a substantial portion of the length of said clip.

25. The clip of claim 16, in combination with a clip applier for applying the clip to the fluid carrying structure.

26. The clip of claim 25, wherein said clip applier includes a magazine adapted to hold a plurality of clips.

27. The clip of claim 16, wherein at least one of said upper support member and said lower support member is enlarged adjacent said distal end of said clip.

28. The clip of claim 16 wherein each of said upper support member and said lower support member is formed of a first leg and a second leg.

29. The clip of claim 28, wherein said first leg and said second leg extend generally parallel to one another from said connector.

30. The clip of claim 29, wherein a gap is formed between said first leg and said second leg, and said gap has a width approximately equal to the thickness of said material.

31. The clip of claim 16, wherein said connector has a maximum connector height in a fourth plane perpendicular to the mid-longitudinal axis and the third plane, said maximum connector height being equal to said to said maximum clip height.

32. The clip of claim 16, wherein said upper support member is connected to an upper portion of said connector and said lower support member is connected to a lower portion of said connector so that said coil windings are unwound when opening said dip.

* * * * *